United States Patent
Berthelsdorf et al.

(10) Patent No.: US 8,315,708 B2
(45) Date of Patent: Nov. 20, 2012

(54) PATIENT DEVICE FOR BIDIRECTIONAL DATA COMMUNICATION WITH AN IMPLANT

(75) Inventors: Richard Berthelsdorf, Newberg, OR (US); Joachim Elsner, Berlin (DE); Dawn Flakne, Portland, OR (US); David Kosokowsky, Lake Oswego, OR (US); Gary Rolison, Eagle Creek, OR (US); Björn Henrik Diem, Berlin (DE); Martin Lang, Weisendorf (DE); Jörn Bungartz, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 395 days.

(21) Appl. No.: 11/514,639

(22) Filed: Aug. 31, 2006

(65) Prior Publication Data

US 2008/0058900 A1    Mar. 6, 2008

(51) Int. Cl.
*A61N 1/08* (2006.01)

(52) U.S. Cl. ........... 607/60; 607/30; 607/31; 607/32; 607/59

(58) Field of Classification Search ........ 607/27, 607/28, 30–32, 59, 60
See application file for complete search history.

(56) References Cited

U.S. PATENT DOCUMENTS

| | | | |
|---|---|---|---|
| 6,308,099 B1 * | 10/2001 | Fox et al. | 607/31 |
| 6,512,954 B2 | 1/2003 | Fox | |
| 2004/0215270 A1 * | 10/2004 | Ritscher et al. | 607/27 |
| 2006/0020290 A1 | 1/2006 | Degroot | |
| 2007/0060967 A1 * | 3/2007 | Strother et al. | 607/31 |

FOREIGN PATENT DOCUMENTS

WO    WO 01/45793    6/2001

OTHER PUBLICATIONS

Kardach, Bluetooth Architecture Overview, Internet Citation, http://grouper.ieee.org/Groups/802/11/Tutorial/905386-WPAN-Bluetooth-Tutorial.pdf, Mar. 1999.
European Search Report dated Sep. 28, 2011 (8 pages).

* cited by examiner

*Primary Examiner* — Niketa Patel
*Assistant Examiner* — Michael D Abreu
(74) *Attorney, Agent, or Firm* — ARC IP Law, PC; Joseph J. Mayo

(57) ABSTRACT

A patient device (PD) for wireless data communication with an implant. The PD can be at least in an unpaired state or a paired state. In the paired state the PD is paired to a specific implant specified by an implant's identification code (IIC). The IIC is stored in PD memory. Automatic pairing of the PD to a specific implant is performed upon receiving an incoming data packet containing an IIC when the PD is in its unpaired state with no valid IIC stored in memory. Thus, the PD is tentatively paired to an implant identified by the IIC contained in the incoming data packet by storing the IIC in the memory. Tentative pairing is cancelled if no further communication occurs within a predetermined period of time. A soft paired state is entered if further data communication does occur.

15 Claims, 2 Drawing Sheets

PATIENT DEVICE FOR BIDIRECTIONAL DATA COMMUNICATION WITH AN IMPLANT

BACKGROUND OF THE INVENTION

1. Field of the Invention

This invention relates generally to a system comprising an implantable electrical medical device such as a cardiac pacemaker, together with an external device that provides a bidirectional telemetric link to the implantable medical device. This invention relates in particular to the functionality of such an external patient device. The patient device comprises a receiver, a memory operatively connected to the receiver, the memory being configured to store code identifying a specific implant (implant's identification code (IID)), a timer and, a control unit operatively connected to the receiver, the memory and the timer.

2. Description of the Related Art

In a system comprising one or more implantable medical devices (IP) and one or more patient devices (PD, also referred to as external device), an implantable medical device and patient device may include transceivers that facilitate bidirectional communications between the devices for home monitoring purposes. For wireless communication in such environment the MICS (Medical Implant Communications Service) frequency band is reserved.

In a system for bidirectional communication each patient device should be assigned to a single implant to prevent multiple patient devices from attempting communication with a single implant. This is particularly important in an area where multiple patient devices are in close proximity (e.g., in a nursing home), and so competition between patient devices may result in failed communications due to interference.

If unidirectional telemetry (i.e. telemetry from implant to patient device) is used, then such assignment is not necessary, as unidirectional telemetry does not require or provide for acknowledgements.

In order to follow the MICS regulations as defined by the FCC and ETSI, when communications are to be established, it is necessary for the patient device to scan the MICS band, to find the Least Interfered-with Channel (LIC), and then to transmit a beacon signal to the implant. Subsequently, the implant must search the band to find the channel on which the patient device is transmitting, and only then may the implant use that channel to transmit its data to the patient device. If periodic communications are desired, time synchrony of the implant and patient device is needed in order to prevent either unnecessary emission by the patient device on the MICS band, or unnecessary receiver activity (thus power consumption by the implant) outside of the time of interest. Therefore, timing information is exchanged between the implant and patient device during their communications.

Presently, assignment is achieved manually by addressing the patient device via the internet and transmitting an implant identification code to the patient device to thus assign the patient device to the implant specified by the implant identification code.

BRIEF SUMMARY OF THE INVENTION

According to the present invention the object of the invention is achieved by a patient device that can be at least in an unpaired state or in a paired state, wherein in its paired state the patient device is paired to a specific implant specified by an implant's identification code that is stored in the memory of the patient device. The control unit is adapted to control automatic pairing of the patient device to a specific implant upon receiving a data packet containing an implant's identification code when the patient device is in its unpaired state with no valid implant identification code stored in the memory prior to receiving the data packet containing the implant identification code. One or more embodiments of the invention allow for the control of a plurality of implants by storing more than one implant identification code in memory.

The control unit tentatively pairs the patient device to an implant identified by the implant's identification code contained in the data packet by storing the implant's identification code in the memory.

When the patient device eventually is tentatively paired to a specific implant, the control unit will either cancel tentative pairing to the implant by deleting the implant's identification code in the memory, if no further data communication is occurring within a predetermined period of time after first receiving the data packet containing the implant's identification code leading to tentative pairing, or maintain a paired state by keeping the implant's identification code in the memory if further data communication is occurring within a predetermined first period of time after first receiving the data packet containing the implant's identification code leading to tentative pairing.

The pairing thus automatically achieved is called "soft pairing" for the purpose of this description. Another type of pairing preferably provided by the patient device is "hard pairing". Whereas a soft paired patient device will return to its unpaired state when no communication between the patient device and the implant the patient device is paired with takes place within a predetermined period of time (that is longer than the period of time for canceling tentative pairing), no such time limit is applicable to hard paired patient devices.

The invention is based on the concept, that a patient device is unambiguously assigned and thus paired to a specific implant identified by its implant identification code. Additionally, an implant does not store assignment information relating to a specific patient device other than the patient device's identification code for mirroring purposes when responding to a data packet originating from the patient device. A patient device can be assigned to no implant or a single implant, but never simultaneously to multiple implants. Thus, the patient device can either be in an unpaired state where it is not assigned to any specific implant or in some paired state wherein the patient device is assigned to a single specific implant. In particular, two paired states are provided, namely a soft paired state resulting from automatic pairing and a manually induced hard paired state. The hard paired state is preferably achieved using a programmer for directly programming a specific implant's identification code IID into the patient device's memory. Hard pairing can also be achieved by sending a pairing message to the patient device over the telephone, the internet, or other means.

In order to eventually receive a data packet originating from an implant and containing an implant identification code, the control unit preferably is adapted to cause the patient device's receiver to periodically or continuously scan or monitor a predetermined wireless communication frequency band or a predetermined channel within the wireless communication frequency band, respectively, for incoming data packets containing an implant's identification code.

Such scanning of a plurality of channels of a wireless communication frequency band may be performed to determine a least used channel within the frequency band and to thereupon send a request data packet using the channel thus determined in order to induce an implant receiving the request data packet to send a response data packet containing the implant's identification code IID.

Therefore, in a preferred embodiment, the control unit is adapted to cause the patient device's receiver to periodically or continuously scan all channels of a predetermined wireless communication frequency band for incoming data packets containing an implant's identification code when the patient device is in its unpaired state.

As a result of pairing, a dedicated channel within the wireless communication frequency band may be determined for future communication between the patient device and the implant the patient device is paired to. Therefore, in particular if the patient device already is in its paired state, it is preferred that the control unit be adapted to cause the patient device's receiver to periodically or continuously monitor a predetermined channel in the wireless communication frequency band for incoming data packets containing an implant's identification code IID.

In a particularly preferred embodiment the patient device's receiver is part of a transceiver, and the control unit is adapted to cause the patient device's transceiver to:

Periodically or continuously scan a predetermined data transmission band for a least used channel Send an outgoing data packet containing the patient device's identification code using the least used channel, and Wait for an incoming data packet in response to the outgoing data packet that contains the patient device's identification code (EID) and an implant identification code (IID).

In order to prevent the patient device from being fooled by data packets sent out by other patient devices, the control unit preferably is adapted to discriminate data packets originating from an implant from data packets originating from other devices. The control unit can be adapted to evaluate a predetermined bit or bits of an incoming data packet in order to determine whether the data originates from an implant or not. In a preferred embodiment, the control unit is adapted to reject pairing when determination of the incoming data packets origin indicates that the incoming data packet does not originate from an implant. Thus, automatic soft pairing can only be induced by an implant itself.

In order to prevent a patient device from pairing itself to an implant that is already in communication with another patient device, the control unit preferably is adapted to cease pairing when the patient device receives an incoming data packet containing a specific patient device identification code (EID) other than the patient device's own patient device identification code EID. Thus, the control unit is adapted only to allow pairing when the patient device receives an incoming data packet containing an unspecific patient device identification code (EID). The unspecific patient device identification code number (EID) preferably is the number zero. Thus, the patient device will only pair in response to reception of a data packet originating from an implant that contains a specific implant identification code IID along with a patient device identification code EID that either is 0 or the receiving patient device's own identification code.

Preferably, means are additionally provided to let the patient device return to its unpaired state. Such means can be a user actuatable means for setting the patient device in its unpaired state, preferably a reset button operatively connected to the control unit, the control unit being adapted to delete the implant's identification code in the memory in response to pressing the reset button. In addition or as an alternative, the patient device can be adapted to reset to its unpaired state by a reset message from a programmer or a customer service centre, communicated via, for example, the telephone or the internet.

In addition or as an alternative, the control unit can be adapted to automatically reset the patient device from its soft paired state to its unpaired state if for a second predetermined period of time (the time for soft pairing to expire) no further incoming data packet containing the stored implant identification code is received, the second period of time being longer than the first period of time (the time for tentative pairing to expire).

Setting the patient device in its unpaired state is preferably achieved by storing an unspecific implant identification code, e.g. IID=0, in the patient device's memory at an address reserved for the implant identification code (IID).

The object of the invention also is achieved by a data packet for use in wireless communication between a patient device and an implant, wherein the data packet contains an implant identification code (IID), a patient device identification code (EID) and an identifier of data packet origin. The identifier of data packet origin preferably is a single origin identifier bit which in its first state, 0 or 1, characterizes a data packet originating from an implant and in its second state, 1 or 0, respectively, characterizes a data packet originating from a patient device.

Messages sent out by an implant may have different levels of priority. Preferably three levels of priority are provided: low, medium and high.

According to a preferred embodiment of the invention, the state of pairing results in treating different kind of messages differently depending on a message's priority as follows:

high-priority messages do not require acknowledgements from the patient device, and thus are unidirectional communications from an implant to any nearby patient device. The patient device will always accept a high priority message from any implant regardless of the state of pairing of the patient device. This is achieved by making the patient device's control unit sensitive to a priority indicator contained in an incoming data packet.

If the patient device is in its hard paired state it will communicate in a bidirectional manner only with the implant that the patient device is assigned to, although even a hard paired patient device will also accept high-priority unidirectional data from any implant, as indicated above.

If the patient device is in its soft paired state it will communicate only with the implant that the patient device is assigned to if an incoming data packet contains data characterizing the incoming message as being a low priority (periodic, bidirectional) message. A soft paired patient device is adapted to communicate with any implant for either medium-priority (bidirectional) or high-priority (unidirectional) messages.

Thus, a preferred patient device will accept:

routine or low-priority messages if the data packet containing the message contains an implant identification code (IID) corresponding to the IID that is stored in the patient device's memory, that is if the routine or low-priority message origins from an implant that the patient device is paired to.

medium-priority messages containing any implant identification code as long as the patient device is in it's soft paired state or is hard paired to the specific implant that the medium-priority message origins from.

any high-priority messages from any implant.

For this purpose, a data packet according to the invention preferably contains a priority indicator.

Accepting a message received by means of an incoming data packet preferably includes storing and forwarding the message to a further device like a central service centre.

Preferably, the patient device is adapted so that it can be interrogated to determine the implant identification code (IID) stored in the patient device's memory and which characterizes the implant that the patient device is paired to. The IID may be, for example, the implant's serial code.

It is a major advantage of a patient device according to the invention, that the pairing is performed by the patient device alone, that is, no action or storing of information is required to be performed by the implant. All pairing means are incorporated into the patient device. This is important, as it allows any implant to pair with any unpaired patient device, and thus to communicate information to the user.

Further preferred embodiments become apparent from the following detailed description of the invention.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
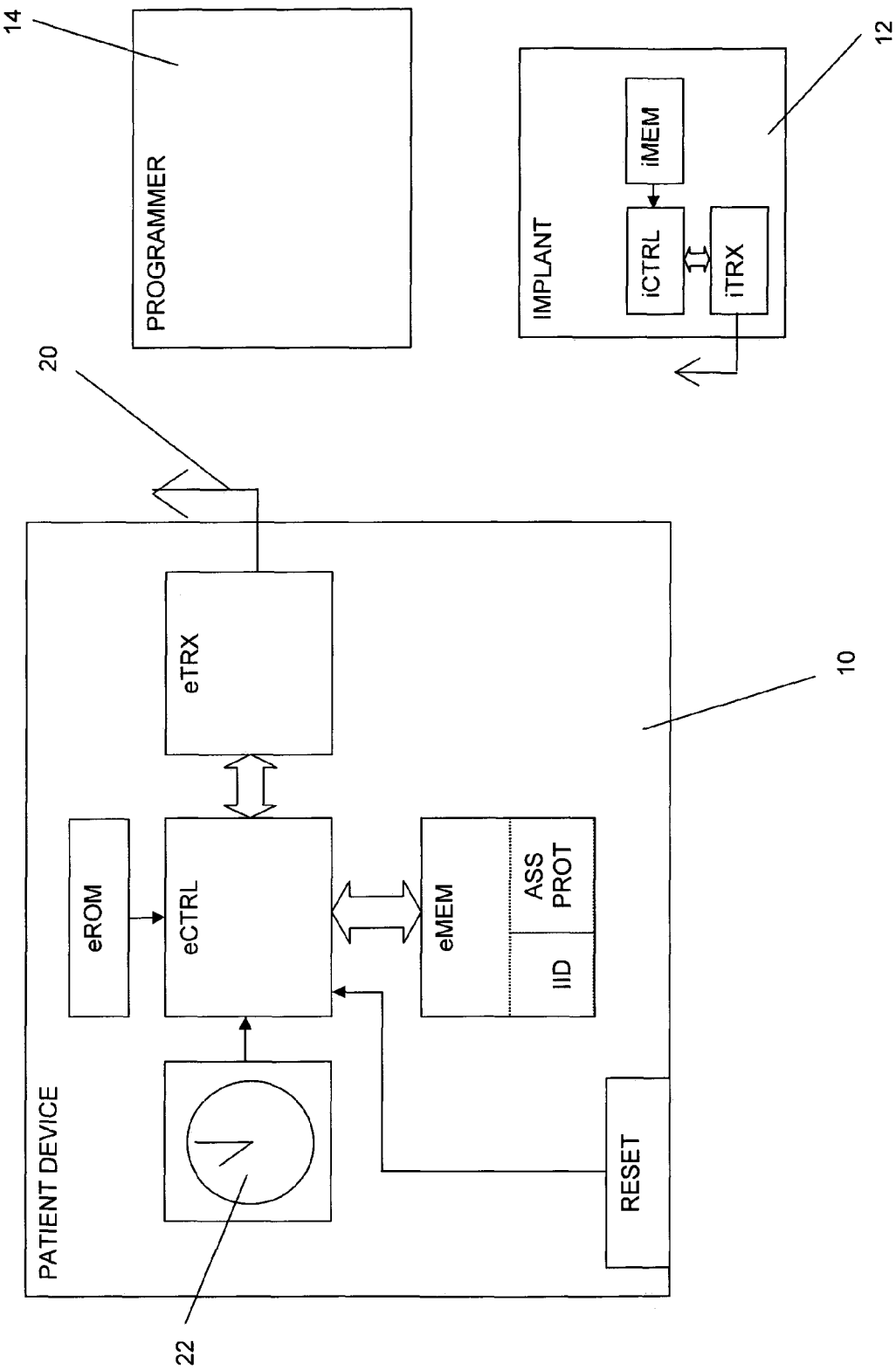
FIG. 1 shows a system comprising an implantable pacemaker, a patient device and a programmer, the patient device being represented by a schematic block diagram showing the main features of the patient device being of importance with respect to a preferred embodiment of the invention.

In FIG. 1, a patient device 10 is depicted in an environment also comprising an implant 12 and a programmer 14.

Patient device 10 is a patient device comprising—among other features of no particular interest for the present invention—a patient device transceiver eTRX, connected to an antenna 20 and to a patient device control unit eCTRL. Control unit eCTRL is connected to a timer 22 and to a patient device memory eMEM. Memory eMEM comprises program or instruction data defining an assignment procedure to be carried out by the control unit eCTRL and the patient device during pairing of patient device 10 to an implant. Memory eMEM also comprises dedicated address space for storing an implant identification code IID.

Control unit eCTRL further is connected to a patient device read only memory eROM comprising the patient devices identification code EID (external device ID).

The implant also comprises a memory iMEM, that preferably is a read only memory ROM for storing an implant identification code IID, a control unit iCTRL connected to the implant's memory iMEM and a transceiver iTRX for bidirectional data communication with the patient device 10.

The tranceiver eTRX of the patient device and of the implant iTRX are both adapted to operate in the MICS band, a wireless communication frequency band reserved for medical implant communications services.

A real world environment may comprise a plurality of patient devices and implants. Therefore, any patient device in such environment shall be assigned to its specific single implant or to no implant at all. Assigning a patient device to an implant is called pairing for the purpose of this description.

Patient device 10 may be in different states of pairing. Patient device 10 may be unpaired, can be soft paired or can be permanently paired (hard paired) to a specific implant. Soft pairing of a patient device to an implant results from automatic pairing, whereas hard pairing of a patient device to an implant results from manual pairing, e.g. via programmer 14.

When in its soft paired state, patient device 10 will return to its unpaired state if for a predetermined period of time no data communication has occurred with the implant that patient device 10 is paired to. For a hard paired patient device, no such period of time is applicable, thus a hard paired patient device is permanently paired to a specific implant.

When patient device 10 is in its unpaired state, patient device 10 also is in a search mode wherein patient device 10 carries out a protocol for automatic pairing. As long as patient device 10 is paired to its specific implant, patient device 10 may be either in a wait mode as long as no data communication is going on with the implant patient device 10 is assigned (paired) to, or in a communication mode during data communication between patient device 10 and the implant patient device 10 is paired to.

As long as patient device 10 is unpaired and therefore is in its search mode, control unit eCTRL causes the patient devices transceiver eTRX to periodically scan the MICS band in order to determine a least used channel. This is called "listen before talk". Thereafter, patient device 10 will use the least used channel to send out a data packet containing the patient device's identification code EID and an unspecific implant identification code IID as is stored in memory eMEM. Since, when in its search mode patient device 10 is in its unpaired state, no or an unspecific implant identification code is stored in the memory eMEM. In the data packet, an origin identifier bit is set in order to mark the data packet as originating from a patient device.

An implant like implant 12 scanning all channels of the MICS bend eventually may receive a data packet originating from patient device 10. If the data packet contains a specific implant identification code IID that does not correspond to the receiving implant's implant identification code IID, then the receiving implant will not respond to such data packet. On the other hand, if the data packet received by the implant contains an unspecific implant identification code IID (e.g. IID=0), the implant will respond to the data packet by sending out a data packet containing the patient device identification code EID as received with the incoming data packet, its implant identification code IID and a origin identifier bit set as to mark a data packet originating from an implant.

If patient device 10 receives such data packet originating from an implant containing the patient device's own identification code EID, such data packet causes patient device 10 to enter its tentatively paired mode and to store the implant identification code IID received with the data package in memory eMEM.

Patient device 10 thereupon will send out a further data packet with its own identification code EID being the specific patient device identification code as stored in patient device's eROM and the origin identifier bit set to "patient device". Thereafter, patient device 10 will wait for a predetermined first period of time for a response data packet from the specific implant patient device 10 is tentatively paired to. If during the predetermined period of time a response data packet is received from the implant the patient device is tentatively paired to, and the response data packet contains the patient device's own identification code, then patient device 10 will enter its soft paired state.

The patient device will stay in its soft paired state as long as a data communication periodically occurs with the implant to which the patient device is paired, and as long as no manual reset of the patient device to its unpaired state occurs.

If for another predetermined period of time, being longer than the first period of time that the patient device will wait until leaving its tentatively paired state no data communication between the patient device and the implant it is paired to occurs, the soft paired state is cancelled and the patient device returns into its unpaired state. This is controlled by timer and control unit eCTRL, and is performed by storing an unspecific implant identification code IID, e.g. IID=0, into memory eMEM of patient device 10.

At any time patient device 10 may be manually reset by pressing reset button RESET, or via other means, e.g., a physician, programmer or via the internet.

Figure 2:
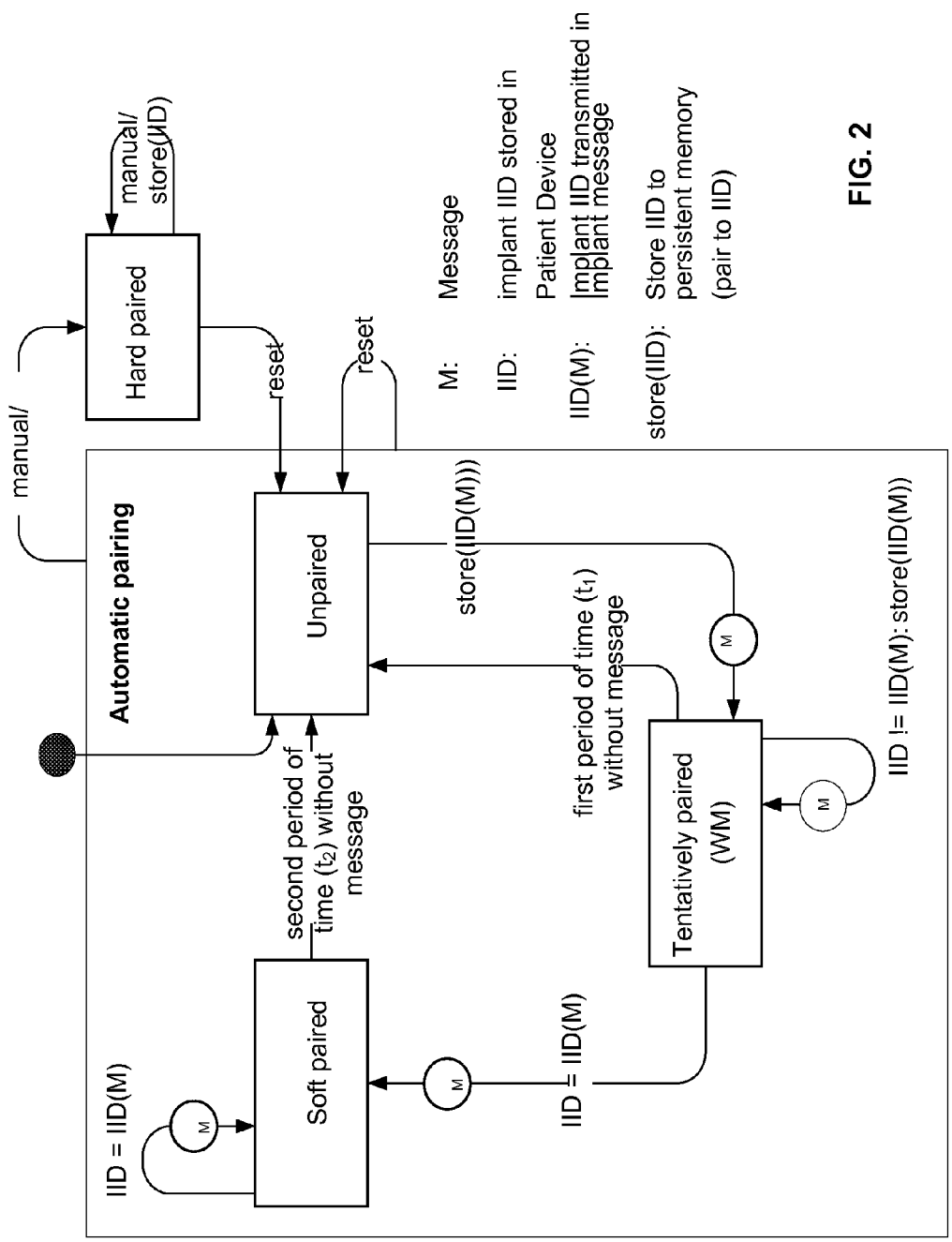
FIG. 2 is a state diagram of the patient device illustrating the functional behavior of the patient device.

For further details of the patient device's behavior with respect to pairing please refer to the state diagram in FIG. 2 and the description above.

Although an exemplary embodiment of the present invention has been shown and described, it should be apparent to those of ordinary skill that a number of changes and modifications to the invention may be made without departing from the spirit and scope of the invention. This invention can readily be adapted to such devices by following the present teachings. All such changes, modifications and alterations should therefore be recognized as falling within the scope of the present invention.

What is claimed is:

1. A patient device for wireless data communication with an implant wherein said patient device comprises:
   a transceiver comprising a first receiver and transmitter configured for data communication wherein said first receiver is configured to receive an incoming data packet from an implant or another patient device and wherein said transmitter is configured to transmit an outgoing data packet to said implant or forward a packet to a further device;
   a volatile memory operatively connected to said first receiver, said volatile memory being configured to store an implant identification code;
   a non-volatile memory operatively connected to said first receiver, said non-volatile memory being configured to permanently store a patient device identification code;
   a timer;
   a control unit operatively connected to said first receiver, said volatile and non-volatile memories and said timer wherein said control unit is configured to
   control said first receiver to scan a predetermined data transmission band for a least used channel;
   control said transmitter to send said outgoing data packet over said least used channel wherein said outgoing data packet contains said patient device identification code and an unspecific implant identification code associated with no implant;
   wait for said incoming data packet having said implant identification code associated with a specific implant and said patient device identification code or an unspecific patient device identification code if said implant transmits said incoming data packet without a specific implant identification code set in said incoming data packet wherein said incoming data packet comprises a priority indicator;
   enter a tentative pairing state for a first predetermined period of time and return to an unpaired state if no further incoming data packet is received within said first predetermined period of time
   and
   enter a soft pairing state if another incoming data packet comprises said patient device identification that is associated with said patient device and not another patient device having a different patient device identification code and if said another incoming data packet comprises a predetermined bit or bits that indicates that said incoming data packet originates from an implant and not said another patient device
   and
   enter said unpaired state if for a second predetermined period of time no further incoming data packet containing said implant identification code is received, said second period of time being longer than said first redetermined period of time;
   respond differently to different incoming data packets, based on said priority indicator contained in said data packets
   and
   accept and to forward each incoming data packet containing a high priority indicator in said priority indicator regardless whether or not said data packet contains said specific implant identification code that is stored in said patient device and regardless of a state of pairing of said patient device.

2. The patient device according to claim 1, wherein said control unit is configured to tentatively pair said patient device to said implant identified by said implant identification code contained in said incoming data packet by storing said implant identification code in said volatile memory and to cancel tentative pairing to said implant by deleting said implant identification code in said memory.

3. The patient device according to claim 1, wherein said patient device comprises a second receiver for receiving programmer commands and wherein said control unit is configured to permanently pair or hard pair said patient device to said implant if said patient device receives a command via said second receiver containing said implant identification code and a hard-pair instruction.

4. The patient device according to claim 1, wherein said control unit is configured to cause said patient device's receiver to periodically or continuously scan or monitor a predetermined wireless communication frequency band or a predetermined channel within said wireless communication frequency band, respectively, for incoming data packets containing said implant identification code.

5. The patient device according to claim 4, wherein said control unit is configured to cause said patient device's receiver to periodically or continuously scan all channels of a predetermined wireless communication frequency band for incoming data packets containing said implant identification code when said patient device is in its unpaired state.

6. The patient device according to claim 4, wherein said control unit is configured to cause said patient device's receiver to periodically or continuously monitor a predetermined channel in said wireless communication frequency band for incoming data packets containing said implant identification code when in said paired mode, said channel being determined during pairing.

7. The patient device according to claim 1, wherein said patient device comprises a user actionable mechanism to set said patient device in said unpaired state.

8. The patient device according to claim 7, wherein said user actionable mechanism is a reset button operatively connected to said control unit, said control unit being configured to delete said implant identification code in said volatile memory in response to pressing said reset button.

9. The patient device according to claim 1, wherein said control unit is configured to set said patient device in its unpaired state.

10. The patient device according to claim 1, wherein said incoming data packet comprises a medium priority indicator and wherein if said patient device is in said soft paired state, then said control unit is configured to accept and to respond to each said incoming data packet containing said medium priority indicator regardless of whether or not said incoming data packet contains said specific implant identification code that is stored in said patient device.

11. The patient device according to claim 1, wherein said incoming data packet comprises a low priority indicator and wherein said control unit is configured to accept and to respond to a data packet containing said low priority indicator only if said incoming data packet contains said specific implant identification code corresponding to said implant identification code stored in said patient device.

12. The patient device according to claim 1 being configured to be paired to at least two implants at said same time, wherein said volatile memory is configured to store at least two implant identification codes.

13. The patient device according to claim 1 wherein said incoming data packet for use in wireless communication between said patient device and said implant comprises:
said implant identification code;
said patient device identification code; and,
an identifier of data packet origin.

14. The patient device according to claim 13 wherein said identifier of data packet origin is a single origin identifier bit which in its first state, 0 or 1, characterizes a data packet originating from an implant and in its second state, 1 or 0, respectively, characterizes a data packet originating from a patient device.

15. The patient device according to claim 13, wherein said incoming data packet further comprises a priority indicator, said priority indicator having at least three different states, a first state thereof corresponding to a low priority, a second state thereof corresponding to a medium priority and a third state thereof corresponding to a high priority.

* * * * *